US010015962B2

(12) United States Patent
Gomez et al.

(10) Patent No.: US 10,015,962 B2
(45) Date of Patent: Jul. 10, 2018

(54) INSECT ATTRACTANT FORMULATIONS AND INSECT CONTROL

(71) Applicant: Dow AgroSciences LLC, Indianapolis, IN (US)

(72) Inventors: Luis Enrique Gomez, Carmel, IN (US); Christina Elizabeth Coen, Grayson, KY (US)

(73) Assignee: Dow AgroSciences LLC, Indianapolis, IN (US)

( * ) Notice: Subject to any disclaimer, the term of this patent is extended or adjusted under 35 U.S.C. 154(b) by 150 days.

(21) Appl. No.: 14/938,676

(22) Filed: Nov. 11, 2015

(65) Prior Publication Data

US 2016/0135451 A1 May 19, 2016

Related U.S. Application Data

(63) Continuation of application No. 13/893,640, filed on May 14, 2013, now abandoned.

(60) Provisional application No. 61/647,322, filed on May 15, 2012, provisional application No. 61/646,565, filed on May 14, 2012.

(51) Int. Cl.
*A01N 31/16* (2006.01)
*A01N 43/22* (2006.01)
*A01M 1/10* (2006.01)
*A01N 37/02* (2006.01)
*A01N 25/10* (2006.01)
*A01N 37/12* (2006.01)
*A01N 45/02* (2006.01)

(52) U.S. Cl.
CPC ............ *A01N 31/16* (2013.01); *A01M 1/106* (2013.01); *A01N 25/10* (2013.01); *A01N 37/02* (2013.01); *A01N 37/12* (2013.01); *A01N 43/22* (2013.01); *A01N 45/02* (2013.01)

(58) Field of Classification Search
CPC ........ A01N 31/16; A01N 37/12; A01N 43/22; A01N 45/02; A01M 1/106
See application file for complete search history.

(56) References Cited

U.S. PATENT DOCUMENTS

| | | | |
|---|---|---|---|
| 4,160,335 | A | 7/1979 | Von Kohorn et al. |
| 5,939,062 | A | 8/1999 | Heath et al. |
| 6,001,346 | A | 12/1999 | Delwhiche et al. |
| 2008/0118461 | A1 | 5/2008 | Boucher, Jr. et al. |
| 2010/0216730 | A1 | 8/2010 | Boucher, Jr. et al. |
| 2011/0290909 | A1 | 12/2011 | White et al. |

FOREIGN PATENT DOCUMENTS

EP 2174546 A1 4/2010

OTHER PUBLICATIONS

Shelly et al. (Florida Entomologist, Dec. 2004, vol. 87, No. 4, 481-486).*
Article: Suspension-Chemistry (obtained online via wikipedia.com on Mar. 27, 2017).*
Article: Emulsion-Chemistry (obtained online via britannica.com on Mar. 27, 2017).*
Hooper, G. H. S. (J. Aust. ent. Soc., 1978, 17: 189-190). (Year: 1978).*
Cheng et al., Instability of the Currently Used Poison Baits for the Oriental Fruit Fly and Melon Fly—The Study on Decomposition of Naled and Cuelure, Jour. Agric. Res. China, 45(4):422-435 (1996).
Special Publication of TARI No. 142: Nonsynthetic Resources for Pest Management, 2010, 139-144.
Extended European Search Report dated Dec. 8, 2015 as received in Application No. 13790401.7.
Leblanc et al., "Evaluation of Cue-Lure and Methyl Eugenol Solid Lure and Insecticide Dispensers for Fruit Fly (*Diptera: Tephritidae*) Monitoring and Control in Tahit", vol. 94, Issue 3, Sep. 1, 2011, pp. 510-516.
T. Shelly., "Field Test Assessing the Performance of Farma Tech Mallet-MC Wafers Against Liquid Male Lures", Jul. 22, 2009, pp. 1-2.
L.L Stelinsky, J.R. Miller, R. Ledebuhr, P. Siegert L. J. Gut, Season-long mating disruption of Grapholita molesta (Lepidoptera: Tortricidae) by one machine application of pheromone in wax drops (SPLAT-OFM), J Pest Sci 2007, 80:109-117.
Ju-Chun Hsu, Pei-Fang Liu, Mark Hertlein, Ronald F. L. Mau, and Hai-Tung Feng, Greenhouse and Field Evaluation of a New Male Annihilation Technique (MAT) Product, SPLAT-MAT Spinosad ME™, for the Control of Oriental Fruit Flies (*Diptera: Tephritidae*) in Taiwan, Formosan Entomology 30: 87-101 (2010).
Todd E. Shelly, Elaine Pahio, Jamed Edu, Synergistic and Inhibitory Interactions Between Methyl Eugenol and Cue Lure Influence Trap Catch of Male Fruit Flies, *Bactrocera dorsalis* (Hendel) and *B. Cucurbitae* (Diptera: Tephritidae), Florida Entomologist, 87(4):481-486. 2004.
Vergas, RI et al. "Methyl eugenol and cue-lure traps for suppression of male oriental fruit flies and melon flies (*Diptera: Tephritidae*) in Hawaii: effects of lure mixtures and weathering." Journal of Economic Entomology. vol. 93, Issue 1 (2000); pp. 81-87.

(Continued)

*Primary Examiner* — Mina Haghighatian
*Assistant Examiner* — Mei Ping Chui
(74) *Attorney, Agent, or Firm* — Yung H. Lee; Barnes & Thornburg LLP

(57) ABSTRACT

An insect control formulation including methyl eugenol, cue lure and a biodegradable wax carrier is a surprisingly effective attractant for Oriental fruit flies (*Bactrocera dorsalis*) and Melon flies (*Bactrocera cucurbitae*). Formulation embodiments that include at least one insect toxicant are surprisingly effective for use in fruit fly MAT attract and kill systems, and are suitable for on-crop or off-crop uses. Formulation embodiments can be provided as aqueous emulsions having viscosities appropriate for use in aerial or backpack spray applications or for delivery using caulk gun-type or grease pump-type devices. Other formulation embodiments can be provided as solid blocks, granules or powders.

16 Claims, 2 Drawing Sheets

(56) References Cited

OTHER PUBLICATIONS

Vargas, RI et al. "Evaluation of SPLAT with spinosad and methyl eugenol or cue-lure for "attract-and-kill" of oriental and melon fruit flies (*Diptera: Tephritidae*) in Hawaii." Journal of Economic Entomology. vol. 101, Issue 3 (2008); pp. 759-768.

Vargas, RI et al. "Attraction and mortality of oriental fruit flies to SPLAT-MAT-methyl eugenol with spinosad." Entomologia Experimentalis et Applicata. vol. 131, Issue 3 (2009); pp. 286-293.

Vargas, RI et al. "Response of melon fly (*Diptera: Tephritidae*) to weathered SPLAT-spinosad-cue-lure." Journal of Economic Entomology. vol. 103, Issue 5 (2010); pp. 1594-1602.

Patent Cooperation Treaty International Search Report and Written Opinion of the International Searching Authority. PCT Patent Application No. PCT/US2013/40901, dated May 14, 2013.

U.S. Appl. No. 13/893,640, filed May 14, 2013.

\* cited by examiner

INSECT ATTRACTANT FORMULATIONS AND INSECT CONTROL

CROSS REFERENCE TO RELATED APPLICATIONS

The present application is a continuation of U.S. patent application Ser. No. 13/893,640 filed 14 May 2013, which claims the benefit of U.S. Provisional Patent Application No. 61/647,322 filed 15 May 2012 and U.S. Provisional Patent Application No. 61/646,565 filed 14 May 2012. The contents of these applications are incorporated herein by reference in their entirety.

BACKGROUND

The present invention provides insect attractant formulations that can be effectively employed to control insect populations using male annihilation technique (MAT), and insect control methods using the formulations. More particularly, the invention concerns a sprayable or solid biodegradable formulation that includes the insect para-pheromones methyl eugenol and cue lure combined with a biodegradable wax carrier. The formulation is effective to provide for continuous release of methyl eugenol and cue lure from the carrier over an extended period of time to effectively attract members of target insect populations. The formulation can be used without an insect toxicant for mating disruption of insect pests. Alternatively, by including at least one insect toxicant in the formulation, the formulation can be used in an "attract and kill" system for controlling insect populations.

Fruit flies (family Tephritidae) are among the most destructive agricultural pests in the world, destroying citrus crops and other fruit and vegetable crops at an alarming rate and forcing food and agriculture agencies to spend millions of dollars on control and management measures. The term "fruit flies" is used herein to indicate all flies belonging to the family Tephritidae (Diptera), examples of which include *Bactrocera dorsalis* (Oriental fruit fly), *Bactrocera cucurbitae* (Melon fly), *Dacus tryoni* (Queensland fruit fly), *Ceratitis capitata* (Mediterranean fruit fly), and fruit flies of the genera *Rhagoletis* and *Anastrepha*, for example.

Fruit flies cause devastating direct losses to many fresh fruits and vegetables. With expanding international trade, fruit flies as major quarantine pests of fruits and vegetables have taken on added importance, triggering the implementation of area-wide national or regional control programs. Damage to fruits and vegetables is caused by fruit fly larvae which tunnel through fruits and in some cases through stem tissue. Bacteria, which are deliberately introduced into the plant host tissue by the adult female fruit fly along with her eggs, multiply at the expense of plant tissue. The larvae then feed on the resultant bacterial "soup" inside the host tissue which is soon rendered unfit for human consumption.

Substantial attention has been given in recent decades to biological control of fruit flies and other insect pests as an alternative to the use of chemical pesticides. Spraying and similar methods of applying crops with chemical pesticides have historically been the most commonly practiced methods of controlling insect pests; however, there are problems with such methods. For example, spraying insecticides typically does not allow targeting of specific types or species of insect pests, which results in destruction of other types or species of insects that may be beneficial to the crop or to the ecological balance of the area being treated. Also, indiscriminant application methods are wasteful of insecticide, and frequent application is generally required, particularly against mobile insect pests. Another disadvantage of widespread aerial spraying of a pesticidal composition is that it generally affects both the agricultural areas and areas inhabited by people, thus also treating non-target species of mammals and arthropods as well as generating adverse environmental effects.

One method of biological control which has proven successful is the use of synthetic insect sex pheromones for pest control by mating disruption. Since much of an insect's behavior is chemically controlled, there is an opportunity to interfere with the natural chemical communication between insects as a means of controlling insect pests. Pheromones are semio-chemicals, i.e., behavior-modifying chemicals, that act as signals to other insects of the same species. Sex and aggregation pheromones are used by a number of different species to locate possible mates. These can be either single components or mixtures of two or more different chemicals that act in concert. Many pheromones have been identified to date, and many of these compounds can be synthetically produced. Synthetically produced compounds that have pheromone-like effect are referred to herein as "para-pheromones." Pheromones and para-pheromones are referred to collectively herein as "attractants." Typically, for mating disruption, a small amount of an attractant is released from a dispenser or carrier material at a level above the concentration released by female insects. When the background level of synthetic pheromone released is above a threshold, male insects are unable to locate female insects. The male's inability to find a mate will then control future populations of the insect pest.

Another method for addressing the disadvantages associated with indiscriminate application of pesticides, which combines features of biological control and pesticide control approaches, involves the use of baits that are adapted to attract particular types and/or species of insects for targeted delivery of insect toxicants. This method enables the selective control of insect pests. An object of this approach is to utilize attractants that selectively draw targeted pests to a lure or trap, while other harmless or beneficial insects in the vicinity are generally not affected. Attractants can be employed in combination with insect toxicants in "attract and kill" systems which utilize the attractants to lure individual insects, typically male insects, of a particular type and/or species to a bait, where the insects then come into contact with an insect toxicant to kill the attracted insects. These types of systems have optimal effectiveness during mating seasons of the insects and optimal effectiveness of such systems relies upon a relatively continuous release of the attractant(s) over an extended period of time, i.e., through typical insect mating periods.

The addition of a pesticide to fruit fly specific attractants is the basis for control by the Male Annihilation Technique (MAT). MAT relies on male fruit flies being strongly attracted to pheromones or pheromone-like chemicals. These pheromones, or analogues thereof, can be used in combination with an insecticide treated matrix to eliminate the males in an area. MAT-based control systems have traditionally used fiber blocks or cotton wads impregnated with cue lure or methyl eugenol (depending on the target species) plus a toxicant to kill the male flies when they are attracted and contact the bait. These 'attract-and-kill' devices generally incorporate high concentrations of the toxicant and cause rapid death of male flies that contact them. The formulated attractant/insecticide can be placed in a large number of traps distributed throughout an area in which control or eradication is desired. MAT works by reducing the male population to an extent that mating is effectively eliminated, or at least substantially reduced. MAT is a proven technique to control fruit flies.

More recently, a variation of the MAT approach has been developed that utilizes a biologically inert matrix for the release of semio-chemicals and/or pesticides. This approach is referred to as "SPLAT" (Specialized Pheromone & Lure Application Technology), and involves the use of a waxy biodegradable carrier that is effective to adhere to plant bark or foliage or other structure present in an area to be treated, then slowly erodes from the surface and biodegrades in the soil during or after the period of time during which the semio-chemicals are released and/or pesticides are dispensed.

The para-pheromones methyl eugenol and cue lure (also referred to as "cuelure") are extremely effective for attracting certain species of insects, but exhibit essentially no attractive effect for other species. For example, fruit flies are very specific in their response to methyl eugenol and cue lure, with prior studies having shown that flies of species that are attracted to methyl eugenol do not respond to cue lure and vice versa. Because the simultaneous attraction of both groups of species would be desirable, attempts have been made to use a mixture of methyl eugenol and cue lure in a single lure or a single fruit fly trap with the objective of providing a system having a broader spectrum of attraction (i.e., attracting fruit flies of more species than are attracted to either methyl eugenol or cue lure individually). Efforts to develop systems utilizing methyl eugenol and cue lure together have not proven successful, however, because cue lure has been consistently shown in multiple reported studies to have an antagonistic or inhibitory effect on the ability of methyl eugenol to attract Oriental fruit flies. Therefore, notwithstanding the benefits such a combination would provide, and notwithstanding efforts to use these two attractants together, cue lure's inhibiting or antagonizing effect on methyl eugenol has prevented the development of combined methyl eugenol and cue lure lures.

SUMMARY

The present invention is based upon the discovery that cue lure can be included together with methyl eugenol in the presence of certain other ingredients to provide an insect attractant formulation that is surprisingly effective for attracting male Oriental fruit flies (which are attracted to methyl eugenol but not cue lure) and Melon flies (which are attracted to cue lure but not methyl eugenol). In particular, combination of methyl eugenol and cue lure with a biodegradable wax carrier, e.g., a sprayable wax carrier as described herein, enables the preparation of a formulation effective to attract a broader spectrum of fruit fly species than formulations including only one of methyl eugenol or cue lure, and exhibits surprising and unexpected fruit fly attraction properties. In one embodiment, a formulation comprising a combination of methyl eugenol and cue lure is effective, contrary to prior expectations and results, for attracting male fruit flies of both *Bactrocera dorsalis* (Oriental fruit fly) and *Bactrocera cucurbitae* (Melon fly).

In one embodiment, a formulation comprises a sprayable wax emulsion having a viscosity appropriate for use in aerial or backpack spray applications and suitable for on-crop or off-crop uses. In various embodiments, a formulation can also include one or more insect toxicant Such a formulation embodiment can be used in a system for control of a target insect population using male annihilation technique (MAT). In one embodiment, the insect toxicant, methyl eugenol and cue lure, and optionally other formulation ingredients, are dispersed and entrapped in an emulsion of biodegradable wax. Another aspect of this disclosure is a method for control of a target insect population which comprises spraying an insect control formulation as described herein at a locus where control is desired. In one embodiment the targeted insect species include Oriental fruit fly and Melon fly, the male-specific attractant comprises a combination of methyl eugenol and cue lure, and the insect toxicant comprises a spinosyn or butenyl spinosyn insecticide.

In another embodiment, a formulation is provided as a solid, such as, for example, a shaped solid block, a plurality of solid granules or a powder. The formulations described herein, whether in the form of a sprayable or flowable emulsion, a sprayable or flowable powder or granule or a solid block, can be incorporated within lures, traps, and other devices used for insect attraction or monitoring, a wide variety of examples of which are widely known and used to control or monitor fruit flies. Alternatively, the formulations can be placed in the field at one or more desired loci without the need for traps. For example, the sprayable or flowable formulations described herein can be applied directly to trees or other structures present in an area to be treated by spraying dollops of the formulation directly on such tree or other structure, by applying a coating of the formulation to a surface of such tree or other structure or by broadcasting a granular or particulate formulation in an area to be treated.

Further embodiments, forms, features, advantages, aspects, and benefits shall become apparent from the following descriptions.

DETAILED DESCRIPTION

Figure 1:
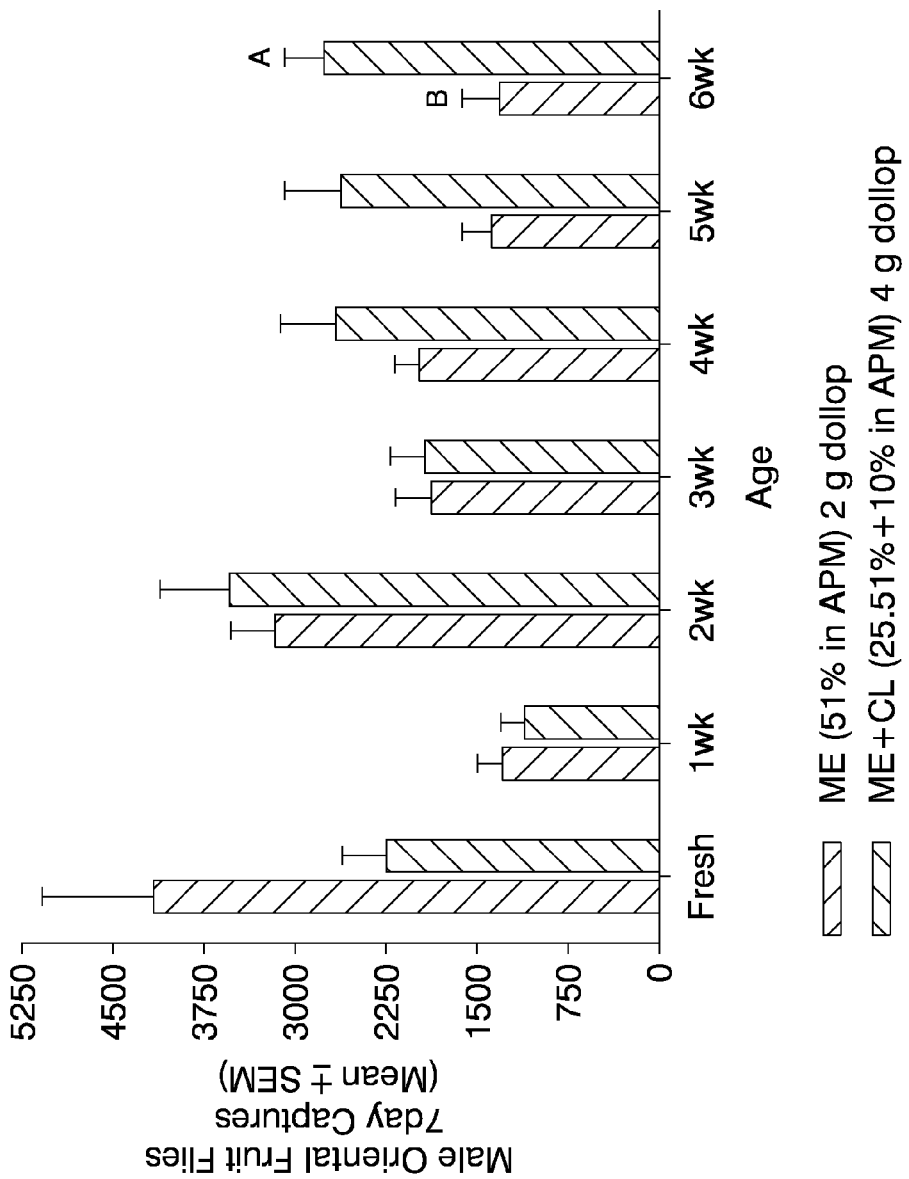
FIG. 1 is a bar graph depicting the number of male Oriental fruit flies captured in traps baited with methyl eugenol (ME alone or methyl eugenol+cuelure (ME+CL) in an amorphous polymer matrix (APM) in the test described in Example III.

For the purpose of promoting an understanding of the principles of the invention, reference will now be made to various embodiments and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Notwithstanding consistent reports in the published literature that cue lure has an inhibitory or antagonistic effect on methyl eugenol as an attractant to male Oriental fruit flies, it has surprisingly been discovered that methyl eugenol and cue lure can be effectively used together as a combined attractant for multiple species of fruit flies when combined with certain other ingredients. Fruit fly attract and kill formulations as described herein have been made and tested and have been discovered to exhibit surprisingly good properties compared to the methyl eugenol and cue lure combinations described in the prior art, and even compared to formulations including only methyl eugenol or only cue lure.

While the most useful application of the subject matter disclosed herein is expected to be in a MAT formulation, and thus formulations are described herein primarily in the context of "attract and kill" systems, alternative applications of attractant formulations are also envisioned, such as, for example, formulations that include a combination of methyl eugenol, cue lure and a biodegradable wax carrier, but do not include insect toxicants. Such a formulation could be used as a fruit fly lure designed to attract fruit flies for a purpose other than contacting the fruit fly with an insect toxicant. Insect attractant formulations without insect toxicants can be used, for example, by researchers, agriculturists, government agencies, and individuals to detect the presence of certain types or species of fruit flies at a given locus, to monitor insect populations, and to kill insects harmful to agricultural crops using modes other than contact with an insect toxicant. Insect attractant formulations can be used in a wide variety of traps, lures, sprays, dollops, coatings and mixtures, and using a wide variety of devices and methods to deploy or deliver them to the desired locus.

In one embodiment, an attractant formulation comprises a combination of methyl eugenol, which is known to attract *Bactrocera dorsalis* (Oriental fruit fly) and other fruit fly species, cue lure, which is known to attract *B. cucurbitae* (Melon fly) and other fruit fly species, and a biodegradable wax carrier effective to provide a substantially continuous release of the methyl eugenol and cue lure over an extended period of time. As indicated above, previous studies have shown that combinations of cue lure and methyl eugenol are less effective as an attractant for Oriental fruit flies than lures including methyl eugenol alone. Such combinations of cue lure and methyl eugenol have therefore become widely viewed as lacking merit because they are no better than cue lure alone at attracting Melon flies and other cue lure-responsive fruit fly species and are inferior to methyl eugenol alone at attracting Oriental fruit flies and other methyl eugenol-responsive fruit fly species. Thus, the combination of cue lure and methyl eugenol is widely regarded as failing its primary objective of controlling methyl eugenol-responsive species and cue lure-responsive species with a single attractant formulation.

However, as employed in the formulations disclosed herein, the combination of methyl eugenol and cue lure surprisingly achieves the dual benefit of attracting Oriental fruit flies and other methyl eugenol-responsive species to a comparable or greater degree than methyl eugenol used alone, and also attracts Melon flies and other fruit fly species that are responsive to cue lure to a comparable degree as cue lure used alone, thus providing a broader spectrum effect than provided by previously known attract and kill formulations. Thus, the formulations described herein represent unexpectedly and surprisingly effective insect attractant formulations utilizing a combination of attractants that previously have been regarded as being unsuitable for use together in a single lure.

The present disclosure therefore enables application of a single formulation including methyl eugenol and cue lure to control insects of methyl eugenol-responsive and cue lure-responsive fruit fly species. This is a significant advance over the prior art, which requires the use of separate formulations to control methyl eugenol-responsive fruit fly species and cue lure-responsive fruit fly species. Thus, a more cost effective and more broadly effective treatment is made possible by this disclosure.

One insect control formulation embodiment includes: (a) methyl eugenol, (b) cue lure, and (c) a biodegradable wax carrier that is effective to provide continuous release of the methyl eugenol and cue lure over an extended period of time. In one embodiment, the extended period of time is a period of at least 3 weeks. In another embodiment, the extended period of time is a period of at least 4 weeks. In yet another embodiment, the extended period of time is a period of at least 4 weeks. In still another embodiment, the extended period of time is a period of from about 4 to about 12 weeks.

In one embodiment, the formulation includes methyl eugenol in an amount from about 0.01% to about 75% by weight of the total formulation, or any weight range within said weight range, and cue lure in an amount of from about 0.01% to about 40% by weight of the total formulation, or any weight range within said weight range. For example, in another embodiment, the formulation includes methyl eugenol in an amount from about 1% to about 60% by weight of the total formulation and cue lure in an amount of from about 1% to about 30% by weight of the total formulation. In yet another embodiment, the formulation includes methyl eugenol in an amount from about 5% to about 45% by weight of the total formulation and cue lure in an amount of from about 1% to about 20% by weight of the total formulation. In still another embodiment, the formulation includes methyl eugenol in an amount from about 10% to about 30% by weight of the total formulation and cue lure in an amount of from about 5% to about 15% by weight of the total formulation. In still yet another embodiment, the formulation includes methyl eugenol in an amount from about 15% to about 25% by weight of the total formulation and cue lure in an amount of from about 5% to about 15% by weight of the total formulation. As used herein, the term "total formulation" refers to all of the ingredients in a given formulation other than water. This term is used in this manner with the understanding that the amount of water included in the emulsion embodiments described herein can vary significantly, which can have an effect on the viscosity of the formulation and the drying time of a coating or dollop of the formulation after application to a locus in the field, but does not otherwise affect the properties or effectiveness of a given formulation. Therefore the values provided in this disclosure as weight percent of a total formulation refer only to the non-water ingredients of the subject formulation.

The term "wax" refers to a class of chemical compounds that are plastic (malleable) near ambient temperatures. Characteristically, they melt above 45° C. (113° F.) to give a low viscosity liquid. Waxes are insoluble in water but soluble in organic, nonpolar solvents. All waxes are organic compounds, both synthetic and naturally occurring.

The biodegradable wax carrier in one embodiment comprises a compound or compounds operable to form an aqueous sprayable emulsion at ambient temperatures of a given treatment locus. In another embodiment the biodegradable wax carrier comprises a compound or compounds operable to form a solid block or solid granule at ambient temperatures of a given treatment locus. In an aqueous sprayable emulsion embodiment, the aqueous emulsion is operable to dry (i.e., upon evaporation of the water from the emulsion) after being placed in ambient conditions to form a dollop or coating with the methyl eugenol and cue lure dispersed and releasably contained in a biodegradable wax carrier matrix. "Spraying" of an aqueous emulsion refers to application of the formulation by spraying, squirting or splatting. "Spraying" of a formulation that is solid at ambient temperature refers to applying the formulation as a granular material to a treated surface or heating the formulation to a flowable state and then applying the formulation to a locus by spraying, squirting or splatting. The methyl eugenol and cue lure are releasably contained in, and then continuously released from, the dollop, coating, block, granule or the like over an extended period of time.

In one embodiment, the biodegradable wax carrier is a wax selected from the group consisting of beeswax, lanolin, shellac wax, carnauba wax, fruit wax (such as, for example, bayberry or sugar cane wax), candelilla wax, hydrocarbon based waxes such as paraffin wax and other waxes such as, for example, microcrystalline, ozocerite, ceresin, montan, vegetable based waxes such as soy wax, or combinations thereof. In one embodiment, the biodegradable wax carrier is present in the formulation in an amount of from about 10% to about 90%, by weight of the total formulation, or any weight range within said weight range. For example, in another embodiment, the formulation includes a biodegradable wax carrier in an amount from about 20% to about 80% by weight of the total formulation. In yet another embodiment, the formulation includes a biodegradable wax carrier in an amount from about 30% to about 70% by weight of the total formulation. In still another embodiment, the formulation includes a biodegradable wax carrier in an amount from about 40% to about 60% by weight of the total formulation.

In one embodiment, the biodegradable wax carrier comprises paraffin wax. Paraffin wax is easy to handle, has a practical melting point for uses as described herein and is relatively inexpensive. Paraffin wax has a melting point in the range of about 50-60° C. (120-140° F.), is nonpolar and miscible with methyl eugenol and cue lure when molten. Paraffin wax also exhibits good continuous release characteristics for the methyl eugenol and cue lure in release rate ranges suitable for the uses described herein. In one embodiment, the paraffin wax used comprises a hexacosane having an average melting point of about 53° C. Formulations including a biodegradable wax carrier comprising paraffin wax can be applied at field temperatures as an aqueous emulsion that adheres to plant bark or foliage, releases methyl eugenol and cue lure for an extended period of time, slowly erodes from plant surfaces and biodegrades in the soil. Alternatively, formulations including a biodegradable wax carrier comprising paraffin wax can be formulated as solid blocks or solid granules in other embodiments. In alternate embodiments, formulations can include paraffin wax alone (i.e., with paraffin wax as the sole biodegradable wax carrier) or in combination with other types of biodegradable carriers, or in combination with a variety of additives, as discussed further below.

In an embodiment in which the biodegradable wax carrier is in the form of an aqueous sprayable emulsion, the carrier can be made as described in U.S. Pat. No. 6,001,346, which is hereby incorporated by reference, and which describes a method for making a biologically inert matrix for the release of semiochemicals and/or pesticides as described herein. Such carriers are available from ISCA TECHNOLOGIES, INC. 1230 W. Spring St., Riverside, Calif. 92507, United States of America under the trademark of SPLAT™ (Specialized Pheromone & Lure Application Technology). In one embodiment, the biodegradable wax carrier is effective to adhere to plant bark or foliage or other structures present in an area to be treated, then slowly erode from the surface and biodegrade in the soil.

In an embodiment useful in an attract and kill fruit fly control system, the formulation also includes one or more insect toxicant (also referred to herein as an "insecticide," each of these terms being used to include a single insecticide or a combination of more than one insecticide in a given formulation). In one embodiment, the insect toxicant is present in an amount from about 0.002% to about 25% by weight of the total formulation, or any weight range within said weight range. For example, in another embodiment, the formulation includes an insect toxicant in an amount from about 0.01% to about 20% by weight of the total formulation. In yet another embodiment, the formulation includes an insect toxicant in an amount from about 0.1% to about 15% by weight of the total formulation. In still another embodiment, the formulation includes an insect toxicant in an amount from about 0.2% to about 10% by weight of the total formulation.

In one embodiment, the insect toxicant comprises a spinosyn natural factor or semi-synthetic derivative or butenyl-spinosyn natural factor or semi-synthetic derivative. Examples of specific spinosyns that can be used include Spinosad and spinetoram.

Spinosad is an insecticide produced by Dow AgroSciences (Indianapolis, Ind.) that comprises approximately 85% spinosyn A and approximately 15% spinosyn D. Spinosyns A and D are natural products produced by fermentation of *Saccharopolyspora spinosa*, as disclosed in U.S. Pat. No. 5,362,634. The spinosyn compounds consist of a 5,6,5-tricyclic ring system, fused to a 12-membered macrocyclic lactone, a neutral sugar (rhamnose), and an amino sugar (forosamine) (see Kirst et al. (1991)). Natural spinosyn compounds may be produced via fermentation from cultures deposited as NRRL 18719, 18537, 18538, 18539, 18743, 18395, and 18823 of the stock culture collection of the Midwest Area Northern Regional Research Center, Agricultural Research Service, United States Department of Agriculture, 1815 North University Street, Peoria, Ill. 61604. Spinosyn compounds are also disclosed in U.S. Pat. Nos. 5,496,931; 5,670,364; 5,591,606; 5,571,901; 5,202,242; 5,767,253; 5,840,861; 5,670,486 and 5,631,155. As used herein, the term "spinosyn" is intended to include natural factors and semi-synthetic derivatives of the naturally produced factors. A large number of chemical modifications to these spinosyn compounds have been made, as disclosed in U.S. Pat. No. 6,001,981, which is also hereby incorporated by reference.

Spinetoram is a semi-synthetic spinosyn insecticide marketed by Dow AgroSciences LLC. Spinetoram (also known as DE-175) is the common name for a mixture of 50-90% (2R,3aR,5aR,5bS,9S,13S,14R,16aS,16bR)-2-(6-deoxy-3-O-ethyl-2,4-di-O-methyl-α-L-mannopyranosyloxy)-13-[(R2R,5S,6R)-5-(dimethylamino)tetrahydro-6-methyl-pyran-2-yloxy]-9-ethyl-2,3,3a,4,5,5a,5b,6,9,10,11,12,13,14,16a,16b-hexadecahydro-14-methyl-1-H-as-indaceno[3,2-d]oxacyclododecine-7,15-dione, and 50-10% (2R,3aR,5aS,5bS,9S,13S,14R,16aS,16b5)-2-(6-deoxy-3-O-ethyl-2,4-di-O-methyl-α-L-mannopyranosyloxy)-13-[(R2R,5S,6R)-5-(dimethylamino)tetrahydro-6-methylpyran-2-yloxy]-9-ethyl-2,3,3a,5a,5b,6,9,10,11,12,13,14,16a,16b-tetradecahydro-4,14-dimethyl-1H-as-indaceno[3,2-d]oxacyclododecine-7,15-dione. Synthesis of the components of spinetoram is described in U.S. Pat. No. 6,001,981.

In another embodiment, the insect toxicant comprises a macrolide insecticide. Macrolide insecticides related to the spinosyns have been isolated from *Saccharopolyspora* sp. LW107129 (NRRL 30141 and mutants thereof). These compounds are disclosed in U.S. Pat. No. 6,800,614, hereby incorporated by reference. These compounds are characterized by the presence of reactive functional groups that make further modifications possible at locations where such modifications were not feasible in previously disclosed spinosyns. Natural and semi-synthetic derivatives of the butenyl spinosyns are disclosed in U.S. Pat. No. 6,919,464, hereby incorporated by reference. The term "butenyl-spinosyn" as used herein is intended to include natural factors and semi-synthetic derivatives of the naturally produced factors.

Spinosyns and butenyl spinosyns are believed to be active against all commercially relevant fruit fly species. Spinosad is approved for use on more than 150 crops. Spinosad has been recognized as an environmentally friendly insecticide, it is used as an organic input and it was a 1999 award winner in the EPAs Presidential Green Chemistry Challenge.

Examples of other insect toxicants that can be used include but are not limited to oranophosphates, such as naled, carbamates, pyrethroids, nicotinics such as imidacloprid or thiacloprid, benzoylphenylureas such as dimilin or novaluron, diacylhydrazines such as methoxyfenozide, phenylpyrazoles such as fipronil or ethiprole, chlorfenapyr, diafenthiuron, indoxacarb, metaflumazone, emamectin benzoate, abamectin, pyridalyl, diamides such as flubendiamide, rynaxypyr (chlorantraniliprole), and cyazypyr (cyantraniliprole), mixes of any of the above or others.

In alternate embodiments, the one or more insect toxicant included in a formulation as described herein can be, for example and without limitation, one or more from the following list: abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, *Bacillus thuringiensis, Bacillus sphaericus,* barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDT, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicam id, flubendiamide (and resolved isomers thereof), flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, fufenozide, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, meperfluthrin, mephosfolan, mercurous chloride, mesulfenfos, metaflumizone, methacrifos, methamidophos, methidathion, methiocarb, methocrotophos, methomyl, methoprene, methothrin, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, profluthrin, promacyl, promecarb, propaphos, propetamphos, propoxur, prothidathion, prothiofos, prothoate, protrifenbute, pymetrozine, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, Spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, and zolaprofos.

In one embodiment, the insecticide included in the formulation is an insecticide approved for use in organic farming. Organic farming methods are internationally regulated and enforced by many nations, based in large part on standards set by international organizations. Examples of naturally-derived insecticides that have been approved for use on organic farms include, for example, *Bacillus thuringiensis*, pyrethrum, Spinosad, neem, and rotenone.

In addition to the ingredients discussed above, a variety of other ingredients can be incorporated into the insect control formulations as optional additives. In one embodiment, an additive comprises an ingredient that either affects the release rate of methyl eugenol and/or cue lure from the formulation or otherwise affects the physical properties of the formulation and/or protect the formulation from weather conditions, for example. Such optional additives include, among others, emulsifiers, plasticizers, volatility suppressants, antioxidants, lipids, various ultraviolet blockers and absorbers, or antimicrobials. In one embodiment, one or more additive is included in the formulation in a total amount of from about 0.001% to about 20% by weight of the total formulation, or any weight range within said weight range. For example, in another embodiment, one or more additive is included in the formulation in a total amount of from about 0.1% to about 10%, by weight of the total formulation. In yet another embodiment, one or more additive is included in the formulation in a total amount of from about 1% to about 6%, by weight of the total formulation.

The additives can be included, for example, in a pre-formulated carrier mixture that includes the biodegradable wax carrier and the additives, which can then be blended with the methyl eugenol, cue lure and, optionally, insect toxicant to provide an insect control formulation. A pre-formulated carrier mixture can be made by combining the carrier mixture and selected additives in predetermined ratios in accordance with the present disclosure, or can be obtained commercially. For example, in one embodiment, the pre-formulated carrier mixture comprises a SPLAT™ matrix, which is commercially from ISCA TECHNOLOGIES, INC. (Riverside, Calif.). In this embodiment, water optionally can be added and mixed into the SPLAT™ matrix prior to, together with or after the methyl eugenol, cue lure and optional insect toxicants are mixed therewith to affect the viscosity of the insect control formulation produced thereby.

Further with regard to additives that can be included in an insect control formulation, in one embodiment, the formulation includes an emulsifier to impart or improve emulsification properties of the formulation. Examples of emulsifiers that can be used in alternate embodiments include lecithin and modified lecithins, mono- and diglycerides, sorbitan monopalmitate, sorbitan monooleate, sorbitan monolaurate, polyoxyethylene-sorbitan monooleate, fatty acids, lipids, and combinations thereof. The emulsifier can be selected from a wide variety of emulsifier products that are well known in the art and available commercially, including but not limited to, sorbitan monolaurate (anhydrosorbitol stearate, molecular formula $C_{24}H_{46}O_6$), ARLACEL 60, ARMOTAN MS, CRILL 3, CRILL K3, DREWSORB 60, DURTAN 60, EMSORB 2505, GLYCOMUL S, HODAG SMS, IONET S 60, LIPOSORB S, LIPOSORB S-20, MONTANE 60, MS 33, MS33F, NEWCOL 60, NIKKOL SS 30, NISSAN NONION SP 60, NONION SP 60, NONION SP 60R, RIKEMAL S 250, sorbitan c, sorbitan stearate, SORBON 60, SORGEN 50, SPAN 55, AND SPAN 60. Other sorbitan fatty acid ester that may be used include sorbitan monostearate, sorbitan tristearate, sorbitan sesquioleate, sorbitan trioleate. In one embodiment, the emulsifier SPAN 60 is included in a formulation.

In one embodiment, an emulsifier is present in the formulation in an amount of up to about 10% by weight of the total formulation, or any range within said range. For example, in another embodiment, the formulation includes an emulsifier in an amount from about 1% to about 10% by weight of the total formulation. In yet another embodiment, the formulation includes an emulsifier in an amount from about 1% to about 6% by weight of the total formulation. In still another embodiment, the formulation includes an emulsifier in an amount from about 1% to about 5% by weight of the total formulation.

Plasticizers can affect physical properties of a formulation described herein, such as, for example, to extend its resistance to degradation in the field. In one embodiment, the insect control formulation includes a plasticizer. Examples of suitable plasticizers include glycerin and soy oil. In one embodiment, a plasticizer is present in the formulation in an amount of up to about 40% by weight of the total formulation, or any range within said range. For example, in another embodiment, the formulation includes a plasticizer in an amount from about 1% to about 40% by weight of the total formulation. In yet another embodiment, the formulation includes a plasticizer in an amount from about 1% to about 25% by weight of the total formulation. In still another embodiment, the formulation includes a plasticizer in an amount from about 1% to about 15% by weight of the total formulation.

In another embodiment, the formulation includes at least one antioxidant that is operable to protect the formulation and/or one or more of its ingredients from degradation. Examples of suitable antioxidants for inclusion include, without limitation, vitamin E, BHA (butylated hydroxyanisole) and BHT (butylated hydroxytoluene). In one embodiment, at least one antioxidant is present in the formulation in an amount of up to about 3% by weight of the total formulation, or any range within said range. For example, in another embodiment, the formulation includes at least one antioxidant in an amount from about 0.1% to about 3% by weight of the total formulation. In yet another embodiment, the formulation includes at least one antioxidant in an amount from about 0.1% to about 2% by weight of the total formulation. In still another embodiment, the formulation includes at least one antioxidant in an amount from about 0.1% to about 1% by weight of the total formulation.

In another embodiment, the formulation further includes at least one ultraviolet blocker effective to protect the formulation and/or one or more of its ingredients from light degradation. Examples of suitable ultraviolet blockers for this use include beta-carotene and p-aminobenzoic acid. In one embodiment, at least one ultraviolet blocker is present in the formulation in an amount of up to about 3% by weight of the total formulation, or any range within said range. For example, in another embodiment, the formulation includes at least one ultraviolet blocker in an amount from about 0.5% to about 3% by weight of the total formulation. In yet another embodiment, the formulation includes at least one ultraviolet blocker in an amount from about 0.5% to about 2% by weight of the total formulation. In still another embodiment, the formulation includes at least one ultraviolet blocker in an amount from about 0.5% to about 1.5% by weight of the total formulation.

In another embodiment, the formulation further includes at least one antimicrobial ingredient to protect the formulation and/or one or more of its ingredients from microbial destruction. Examples of suitable antimicrobial ingredients include potassium sorbate, nitrates, nitrites, 1,2-benzisothiazolin-3-one (biocide ingredient in Proxel® GXL; available from Arch Chemicals, Inc.) and propylene oxide. In one embodiment, at least one antimicrobial ingredient is present in the formulation hi an amount of up to about 3% by weight of the total formulation, or any range within said range. For example, in another embodiment, the formulation includes at least one antimicrobial ingredient in an amount from about 0.1% to about 3% by weight of the total formulation. In yet another embodiment, the formulation includes at least one antimicrobial ingredient in an amount from about 0.1% to about 2% by weight of the total formulation.

Other compounds and materials may also be included in formulations described herein provided they do not substantially interfere with the attractant activity of the formulation. Whether or not an additive substantially interferes with the attractant activity can be determined by standard test formats, involving direct comparisons of efficacy of a given formulation without an added compound or material and a formulation that is otherwise the same, but with the added compound or material.

For example, additional bioactive ingredients can also be included in a formulation as described herein. The term "additional bioactive compound" is used herein to refer to compounds, other than those described above, that fall within one or more of the following categories: attractants, juvenile hormones, plant hormones, pesticides, fungicides, herbicides, nutrients, micronutrients, bacteria (such as *Bacillus thuringiensis*), insect pathogenic virus (such as celery looper virus), fertilizers, plant mineral supplements, or other ingredients that can be included in the formulation to meet specific needs of crop production. For example, the additional bioactive ingredient can include one or more additional male-specific attractants for a variety of additional potential target species, many of which are known and available commercially. Examples include but are not limited to: attractants for Malaysian fruit fly (*Bactrocera latifrons*), including, for example, latilure; for jointed pumpkin fly (*Dacus vertebrates*), including, for example, Vert-lure; for medfly (*Ceratitis capitata*), including, for example, trimedlure or ceralure; for walnut husk fly (*Rhagoletis completa*), including, for example, alpha copaene; for olive fruit fly (*Bactocera oleae*), including, for example, spiroketal. In one embodiment, one or more additional bioactive ingredient is included in an amount up to about 20% by weight based on the total formulation, or any range within said range. For example, in another embodiment, one or more additional bioactive ingredient is included in an amount up to about 10%, by weight. In yet another embodiment, one or more additional bioactive ingredient is included in an amount up to about 5%, by weight.

In yet another embodiment, the formulation also includes a visual attractant, such as, for example a food coloring or other coloring agent, a wide variety of which are known and available commercially. Other ingredients, such as, for example, adjuvants, humectants, viscosity modifiers can also be included.

The components of formulations described herein can be mixed in any manner known in the art. For example, a formulation can be prepared by mixing a predetermined amount of the biodegradable wax, i.e. paraffin wax, with a predetermined amount of water, and then adding predetermined amounts of methyl eugenol and cue lure. (Each "predetermined amount" is based upon the desired ratios of the various components in the final binder formulation).

Optional additional ingredients (i.e., additives) can also be added in predetermined amounts at any stage of mixing. The ratios of the ingredients selected based on the intended properties of the formulation, the intended application method, and other considerations.

In one manner of preparing the formulation, the wax is first heated, under constant stirring, to a melting point temperature, typically from about 40° C. to about 80° C., preferably from about 50° C. to about 60° C., depending on the type of the wax. The methyl eugenol and cue lure, and optionally additional ingredients, alone or in combination, are then added directly to the molten wax carrier and the mixture is stirred. Additional water, or emulsifiers, if needed for emulsification, are added to form the final formulation. The formulation may be stirred or emulsified mechanically. The formulation is then cooled and stored as an aqueous emulsion, or the wax is molded into solid bodies, such as, for example, disk dispensers, or formulated as granules or powders.

As described above, in one manner of making an insect control formulation a pre-formulated carrier mixture including a biodegradable wax carrier and optional additives is first made (i.e., as described in the preceding paragraph) or otherwise provided, and then mixed with the methyl eugenol, cue lure, optional insect toxicant and optional additional water to provide an insect control formulation.

The rate at which methyl eugenol and cue lure are released from the formulation in use (referred to as the "release rate") can be adjusted by inclusion of one or more of the optional additives described above in the formulation. Plant growth and protection can be enhanced in various embodiments by optional addition of other bioactive agents as discussed above. In one manner of employing a formulation as described herein, the formulation, either in the sprayable or solid form, is applied directly to or on the areas or surfaces to be treated, such as orchards, gardens, plants, trees or soil, or other structure in or adjacent to an area to be treated. The sprayable emulsion embodiments can be applied to form a dollop or coating on the treated surface from which the methyl eugenol and cue lure is released in a substantially continuous manner over an extended period of time. In other embodiments, the formulation is applied as a solid composition, such as a disk, granule or powder that is operable to continuously release the methyl eugenol from the solid biodegradable wax carrier matrix over an extended period of time.

Using a variety of additives for control of the release rate from the biodegradable wax carrier, the formulation can be custom designed. In one embodiment, the amount of the methyl eugenol and cue lure to be included in the formulation is calculated to be sufficient to provide insect control during the mating season(s) and/or for a predetermined period of time during which protection is needed or desired. The release rate of the methyl eugenol and cue lure from the biodegradable wax carrier can be affected, for example, by the physical properties of the biodegradable wax carrier, by the respective concentrations of the biodegradable wax carrier, the methyl eugenol, the cue lure and other optional ingredients, and their ratios, by the physical properties and characteristics of the overall formulation, by the presence or absence of one or more optional additives, by the additives' type and concentration, by the application conditions, by the weather and by the season. For example, the thickness of the dollop or coating layer affects the release rate. For example, a slower release rate can be achieved when the formulation is applied as a thicker dollop or coating, by including certain additives in the formulation, by including lower concentrations of the methyl eugenol and/or cue lure, or by providing thicker paraffin wax disks or bigger granules. Conversely, a faster release rate can be achieved with formulations including only a wax carrier without additives, having higher concentrations of the methyl eugenol and/or cue lure, and applied as thin coatings, larger area disks, or smaller granules.

With regard to the effect of additives on the release rate, the release rate of the methyl eugenol and cue lure can also be affected by the presence of certain additives, such as antioxidants and/or volatility suppressants, incorporated into the biodegradable wax carrier together with the methyl eugenol and cue lure. Volatility suppressants decrease the release rate of the attractants. Antioxidants such as vitamin E increase the stability of the attractants and slow their degradation and oxidation. Consequently, a formulation embodiment including these additives can be more economical and can have an improved longevity over embodiments in which the attractants are unprotected and may be subjected to oxidation.

All the above-listed parameters are variable and their variation provides formulations having different release rates of methyl eugenol and cue lure and different useful lives (also referred to as "longevities," which refers to the period of time during which the formulation continues to release effective amounts of methyl eugenol and cue lure). All variations of these properties are intended to be within the scope of the present disclosure.

Another aspect of the present disclosure relates to methods for control and management of fruit flies. Such control is achieved by delivering or applying a formulation as described herein to a locus, such as, for example, a potentially infested area to be protected or an infested area where fruit flies need to be controlled, such as by eradication or the reduction of their numbers to acceptable levels. In one embodiment, the formulation is applied to such area in an amount of from about 0.05 to 1.0 kilograms per hectare. Treatments can include evenly spraying the total amount of product in an area in large dollops (1-4 grams of product) placed on the plants or other surfaces within an orchard. Another manner of treatment includes placing an amount of formulation in traps. Yet another manner of treatment is by spraying or otherwise applying the formulation in an area surrounding an orchard or other area to be treated to avoid leaving residues of formulation components on the crop itself. Because the biodegradable wax carriers described herein are themselves biologically inactive and are subsequently biodegraded without causing any residual environmental or safety hazard, the formulations described herein are safe and non-phytotoxic and are thus suitable for direct contact with trees of fruit orchards and other crops. The formulations described herein do not require any additional handling other than the original application. No removal of containers or washing of residues is necessary. Application does not require special equipment.

In one embodiment, which currently represents the best mode of practicing the method, an insect control formulation as described herein is provided as an aqueous suspension or emulsion, which is sprayed directly on trees, plants or other structures (such as utility poles or the like) in a selected treatment area. For formulations having relatively lower viscosities, this can be achieved by using common types of agricultural sprayers. Relatively higher viscosity formulations can be applied using other devices useful for squirting highly viscous materials. Examples of such devices include commercial grease pumps and caulk guns, which can be readily adapted for delivery of dollops of an insect control formulation as described herein. In one embodiment, the formulation is applied using an aerial or backpack spray device. In other embodiments, the formulation is applied using a caulking gun type device or grease pump type device. When using a delivery device of the caulking gun type or grease pump type, the formulation can be packaged and provided in tubes configured to fit with the delivery device. As is evident from the present disclosure, the formulations can be made to have a wide range of viscosities. In one embodiment, the formulation is applied directly to vegetation. The emulsion formulations described herein can be sprayed or squirted from ground level and thus applied to a higher surface, such as in a tree or other relatively tall structure, than would be convenient for a worker to reach to hang a conventional plastic fruit fly trap or other dispenser.

After an insect control formulation in the form of an aqueous suspension or emulsion is applied to a treated surface (also referred to as a sprayed surface), the water from the emulsion evaporates, resulting in an adherent dried dollop or coating with the methyl eugenol and cue lure distributed within the biodegradable wax carrier (also referred to as a biodegradable wax carrier matrix"). The methyl eugenol and cue lure, and any additional attractants optionally included in the formulation, are continuously released from the matrix over an extended period of time either by diffusing to the surface of the dried dollop or coating where it evaporates, or by degradation or erosion of the matrix. The attractants are released at a rate sufficient to attract members of the targeted type(s) and/or species of fruit flies. In one embodiment, the rate of release is about the same as or above the level of pheromone naturally released by the female insect of the same type or species.

In another embodiment, a formulation as described herein is provided as solid blocks or granules or powders, and the blocks or granules or powders are applied to a locus or multiple loci in a treatment area by placing the blocks or granules or powders on or adjacent to trees or plants in a treatment area. The blocks or granules or powders can be placed in fruit fly traps if desired, but the use of traps is not necessary. Alternatively, the blocks or granules or powders can be placed directly on tree or plant structures or spread on the ground in the treatment area. This can be achieved, for example, by using common types of agricultural spreaders.

Use of formulations as described herein provides flexibility with respect to the amount of the formulation to apply per unit area. That is, depending on the concentrations of various ingredients in the formulation, a fixed quantity of the formulation can be applied differently depending on the pest population pressure or the desired objective in a given area. The application of the formulation can be tailored by the user to best match the pest distribution and density in the field. Using a fixed amount of a given formulation embodiment per area, one can choose, for example, to apply the formulation with a high density of small point-sources, thus maximizing the mating disruption effect (recommended for high pest pressure); or with a low density of larger point-sources, thus increasing the longevity of the application (recommended for lower pest population pressure).

The formulations described herein, once applied, provide long lasting point sources that are spatially discrete, attract targeted pest insects, and provide effective control without having a substantial negative effect on non-target organisms.

As will be appreciated by a person skilled in the art in view of the above descriptions, in one aspect the present disclosure provides an insect control formulation that includes: (i) methyl eugenol; (ii) cue lure; and (iii) a biodegradable wax carrier, in which the methyl eugenol and the cue lure are dispersed in the biodegradable wax carrier and the biodegradable wax carrier is operable to release the methyl eugenol and cue lure over a period of time extending at least four weeks. In one embodiment, the methyl eugenol is from about 1% to about 60% of the formulation by weight, the cue lure is from about 1% to about 30% of the formulation by weight and the biodegradable wax carrier is from about 10% to about 90% of the formulation by weight. Also provided is a formulation in accordance with any of the embodiments described herein which further includes water; in which the formulation comprises a fluid suspension including solid particles of the biodegradable wax carrier suspended in the water, and wherein the methyl eugenol and the cue lure are entrained in one or both of the solid particles and the water. In one embodiment, the methyl eugenol is from about 5% to about 45% of the formulation by weight, the cue lure is from about 1% to about 20% of the formulation by weight, and the biodegradable wax carrier is from about 20% to about 80% of the formulation by weight. Also provided is a formulation in accordance with any of the embodiments described herein in which the fluid suspension is in the form of an emulsion. Also provided is a formulation in accordance with any of the embodiments described herein in which the formulation further includes one or more insect toxicant. In one embodiment, the methyl eugenol is from about 1% to about 60% of the formulation by weight, the cue lure is from about 1% to about 30% of the formulation by weight, the biodegradable wax carrier is from about 10% to about 90% of the formulation by weight; and the one or more insect toxicant is from about 0.002% to about 25% of the formulation by weight. The insect toxicant can be, for example, Spinosad, although a wide variety of other insect toxicants are also contemplated as described herein.

Also provided is a formulation in accordance with any of the embodiments described herein in which the formulation is in the form of an emulsion comprising solid particles of the biodegradable wax carrier suspended in the water, and the methyl eugenol and the cue lure are entrained in one or both of the solid particles and the water. The wax carrier in any of the embodiments described herein can comprise a member selected from the group consisting of paraffin wax, carnauba wax, beeswax, candelilla wax, fruit wax, lanolin, shellac wax, bayberry wax, sugar cane wax, microcrystalline wax, ozocerite, ceresin, montan wax, and combinations thereof. For example, the biodegradable wax carrier can comprise paraffin wax or can consist essentially of paraffin wax. In any of the above embodiments, the wax carrier can be present in an amount from about 20% to about 80% by weight.

In any of the embodiments described herein, the formulation can further comprise one or more additives selected from the group consisting of lipids, emulsifiers, plasticizers, UV blockers and absorbers, antimicrobials, antioxidants and volatility suppressants. For example, the one or more additives can be present in an amount from about 0.001% to about 20% by weight, or in an amount from about 0.1% to about 10% by weight. In any of the embodiments described herein, the additive can comprise an emulsifier in an amount up to about 10% by weight of the formulation. For example, the additive can comprise an emulsifier selected from the group consisting of lipids, soy oil, lecithins, modified lecithins, monoglycerides, diglycerides, sorbitans, and fatty acids, and combinations thereof. In any of the embodiments described herein, the additive can comprise an antioxidant in an amount of from about 0.1% to about 3% by weight of the formulation. For example, the antioxidant can comprise a member selected from the group consisting of vitamin E, butylated hydroxyanisole, and butylated hydroxytoluene. In one embodiment, the formulation comprises an emulsion that includes from about 20 to about 80% by weight of paraffin wax, from about 5% to about 45% by weight of methyl eugenol, from about 1% to about 20% by weight of cue lure, and from about 0.001% to about 10% by weight of one or more additive selected from the group consisting of emulsifiers, plasticizers, and antioxidants combined. In any of the embodiments described herein, the formulation can further include at least one additional bioactive ingredient. For example, the formulation can include at least one additional insect attractant.

Also provided is a formulation in accordance with any of the embodiments described herein in which the formulation is an emulsion and the emulsion is sprayable, squirtable or spreadable. Also provided is a formulation in accordance with any of the embodiments described herein in which the biodegradable wax carrier forms a solid block, granule or powder comprising a porous matrix structure, and wherein the methyl eugenol and the cue lure are entrained within the body.

In one embodiment, an insect control formulation includes from about 5% to about 45% methyl eugenol by weight of the formulation, from about 1% to about 20% cue lure by weight of the formulation, from about 20% to about 80% a biodegradable wax carrier by weight of the formulation and from about 0.1% to about 20% insect toxicant by weight of the formulation; the insect toxicant is selected from Spinosad and spinetoram; the formulation comprises a sprayable emulsion; the methyl eugenol, the cue lure and the insect toxicant are dispersed in the biodegradable wax carrier; and the biodegradable wax carrier is operable to release the methyl eugenol and cue lure over a period of time extending at least four weeks.

In another aspect, the present disclosure provides a method for making an insect control formulation that includes: (i) providing a heated wax carrier; (ii) blending methyl eugenol and cue lure into the heated wax carrier to provide a blended mixture comprising at least about 10% by weight of the wax carrier, from about 0.01% to about 75% by weight of the methyl eugenol, and from about 0.01% to about 40% by weight of the cue lure; and (iii) mixing water into the blended mixture to produce an aqueous emulsion. In one method embodiment, the wax carrier comprises a member selected from the group consisting of paraffin wax, carnauba wax, beeswax, candelilla wax, fruit wax, lanolin, shellac wax, bayberry wax, sugar cane wax, microcrystalline wax, ozocerite, ceresin, montan wax, and combinations thereof. Also provided is a method in accordance with any of the embodiments described herein in which the paraffin wax is present in an amount from about 10% to about 90% by weight, the methyl eugenol is present in an amount from about 5% to about 45% by weight, and the cue lure is present in an amount from about 1% to about 20% by weight. Any of the methods described herein can also include incorporating into the heated wax carrier, the blended mixture or the aqueous emulsion one or more additives selected from the group consisting of lipids, plasticizers, UV blockers and absorbers, antimicrobials, antioxidants, and volatility suppressants. Also provided are methods in accordance with any of the embodiments described herein in which the emulsion is operable to release the methyl eugenol and the cue lure from the wax carrier for a period of time of at least about three weeks, for a period of time of at least about four weeks, or for a period of time of at least about six weeks. Any of the methods described herein can also include incorporating into the heated wax carrier, the blended mixture or the aqueous emulsion at least one member selected from the group consisting of emulsifiers and insect toxicants.

In another aspect, the present application provides a method for controlling one or more fruit fly species that includes: (i) placing in a locus to be treated an insect control formulation comprising methyl eugenol, cue lure and a biodegradable wax carrier; and (ii) bringing a plurality of male fruit flies attracted by one or both of the methyl eugenol and the cue lure into contact with an insect toxicant at the locus. In one embodiment, the formulation comprises the insect toxicant. Also provided is a method in accordance with any of the embodiments described herein in which the formulation is placed in a fruit fly trap positioned in a treatment area. Also provided is a method in accordance with any of the embodiments described herein in which the formulation comprises an emulsion and in which the method includes spraying the formulation onto a structure present in a treatment area. In any of the embodiments described herein, the formulation can comprise or consist essentially of: (a) an insect toxicant, wherein the insect toxicant is from about 0.002% to about 25.00% by weight of the formulation; (b) methyl eugenol, wherein the methyl eugenol is from about 1% to about 60% by weight of the formulation; (c) cue lure, wherein the cue lure is from about 1% to about 30% by weight of the formulation; (d) a biodegradable wax carrier, wherein the biodegradable wax carrier is from about 10% to about 90% by weight of the formulation; and (e) an emulsifier, wherein the emulsifier up to about 10% by weight of the formulation. In any of the methods described herein, the insect toxicant can comprise a member selected from the group consisting of Spinosad and spinetoram. In any of the methods described herein, the amount of insect toxicant can be from about 0.1% to about 15% by weight of the formulation, the amount of methyl eugenol can be from about 5% to about 45% by weight of the formulation, the amount of cue lure can be from about 1% to about 20% by weight of the formulation, the amount of biodegradable wax carrier can be from about 30% to about 70% by weight of the formulation and/or the amount of emulsifier can be from about 1% to about 6% by weight of the formulation.

In any of the embodiments described herein, the method can include applying an effective amount of the insect control formulation over an area to be treated. In any of the embodiments described herein, the applying can comprise spraying. In any of the methods described herein, the method can include applying the formulation to an area to control fruit flies in an amount sufficient to control such pest. The fruit flies can include any fruit fly species that is attracted to one or both of methyl eugenol and cue lure. For example the fruit fly species can be any species in the family Tephritidae, such as, for example, a fruit fly species selected from *Bactrocera carambolae*, *Bactrocera caryeae*, *Bactrocera correcta*, *Bactrocera dorsalis*, *Bactrocera invadens*, *Bactrocera kandiensis*, *Bactrocera occipitalis*, *Bactrocera papayae*, *Bactrocera philippinensis*, *Bactrocera umbrosa*, *Bactrocera zonata*, *Bactrocera cucurbitae*, *Bactrocera cucumis*, *Bactrocera tryoni*, and *Bactrocera tau*. In one embodiment, the fruit fly species is selected from *Bactrocera dorsalis* and *Bactrocera cucurbitae*, and in another embodiment, the fruit fly species is *Bactrocera dorsalis*.

In another aspect, the present disclosure provides a trap for catching fruit flies that includes a container defining a chamber and having an opening to allow fruit flies to enter the chamber and being adapted to substantially restrict fruit flies from exiting the chamber; and an insect-attracting formulation positioned within the chamber, the formulation comprising methyl eugenol, cue lure and a biodegradable wax carrier. In other embodiments, the formulation can be a formulation in accordance with any of the embodiments disclosed herein.

Reference will now be made to the following Examples. The Examples are intended to be illustrative, are provided solely to promote a full understanding of the concepts embodied in the disclosure, and are not intended to be limiting or otherwise restrictive as to the nature and scope of the disclosure.

Example I

To prepare a formulation, a biodegradable wax carrier (e.g., paraffin wax or microcrystalline wax) is heated to a liquid state and thoroughly mixed with attractants (i.e., methyl eugenol, cue lure and optionally additional attractants) and water to form an emulsion. An effective amount of emulsifiers (e.g., sorbitan monostearate), preservatives, antioxidants, UV stabilizers, an insect toxicant (e.g, Spinosad or spinetoram), and/or an effective amount of an insect visual attractant (e.g., green food coloring obtainable from McCormick & Co., Hunt Valley, Md.) are then optionally blended into the emulsion. The mixture is then cooled or allowed to cool. Once the formulation reaches room temperature it is transferred into final packaging.

In an alternative manner of making a formulation, a pre-formulated carrier mixture including the biodegradable wax carrier and optionally including one or more additives (i.e., water, emulsifiers, preservatives, antioxidants, UV stabilizers, insect visual attractants and the like) is made or obtained, and then methyl eugenol, cue lure and an insect toxicant are mixed into the pre-formulated carrier in predetermined proportions selected in accordance with the present disclosure. Water can optionally be added also to affect the viscosity and/or emulsion properties of the formulation. One example of a suitable pre-formulated carrier mixture is a SPLAT™ matrix, which is commercially from ISCA TECHNOLOGIES, INC. (Riverside, Calif.).

Example II

Three formulations (I-III) were made by mixing the components in the proportions indicated in Table 1 at room temperature using a spatula. The pre-formulated carrier mixture emulsion was made in accordance with U.S. Pat. No. 6,001,346.

TABLE 1

| | I | II | III |
|---|---|---|---|
| Pre-formulated Carrier Mixture Emulsion (SPLAT ™ Matrix) (including paraffin wax, water and other additives) | 47% | 62.5% | 78% |
| Spinosad | 2% | 2% | 2% |
| Methyl Eugenol | 51% | 25.5% | 0 |
| Cue Lure | 0 | 10% | 20% |

Example III

The efficacy of formulations I-III of Table I were tested at multiple papaya field locations in an outdoor setting under ambient Hawaii weather conditions. Dollops (2 g each) of formulations I and III and dollops (4 g each) of formulation II were placed in fruit fly traps in a 100-acre papaya field in Keaau, Hi. The trial design was a randomized complete block with four traps per treatment. The 100-acre field was divided in four blocks and one trap per formulation was placed in each block having a distance of a minimum of 100 ft from each other. Traps within each block were rotated clockwise one position every week to compensate for positioning effects within the blocks. Traps containing the formulations were kept in the field for 6 weeks under normal environmental conditions (light, temperature, rain, etc). The formulations were allowed to age under normal conditions and the number of fruit flies in each trap were scored each week for six weeks.

Figure 2:
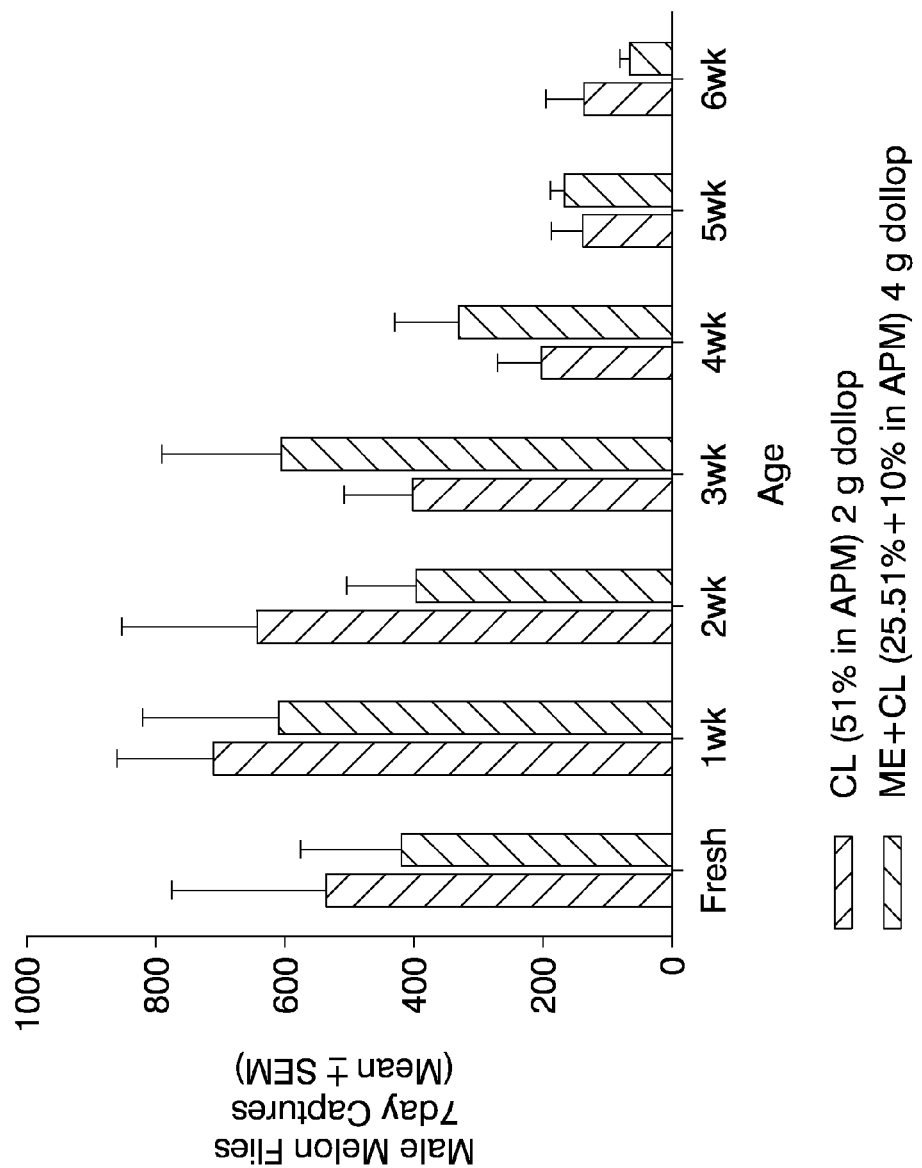
FIG. 2 is a bar graph depicting the number of male Melon flies captured in traps baited with cuelure (CL) alone or methyl eugenol+cuelure (ME+CL) in an amorphous polymer matrix (APM) in the test described in Example III.

The results are set forth in FIGS. 1 and 2. FIG. 1 depicts the number of male Oriental fruit flies captured in traps baited with methyl eugenol (ME) alone or methyl eugenol+ cuelure (ME+CL) in an amorphous polymer matrix (APM) in the test described above. Captures of Melon fruit flies (responsive only to CL) in the traps containing ME alone were 0, and therefore not included in the graph set forth in FIG. 1. FIG. 2 depicts the number of male Melon flies captured in traps baited with cuelure (CL) alone or methyl eugenol+cuelure (ME+CL) in an amorphous polymer matrix (APM) in the test described above. Captures of Oriental fruit flies (responsive only to ME) in the traps containing CL alone were 0, and therefore not included in the graph set forth in FIG. 2. The letters A and B in FIG. 1 represent results that are significantly different $\alpha=0.05$. Formulation II, which includes both methyl eugenol and cue lure, demonstrated practical utility for Oriental fruit fly control and Melon fly control through six weeks of evaluation.

FIG. 2 shows that traps containing formulation II (which includes both methyl eugenol and cue lure as attractants) attracted and captured similar numbers of Melon flies as traps containing formulation III (which includes cue lure alone as the attractant) through six weeks of evaluation. The most surprising result of this experiment, however, is seen in FIG. 1, where it is shown that traps containing formulation II (which includes both methyl eugenol and cue lure as attractants) attracted and captured similar numbers of Oriental fruit flies as traps containing formulation I (which includes methyl eugenol alone as the attractant) through five weeks of evaluation, and attracted and captured significantly greater numbers of Oriental fruit flies compared to traps containing formulation I during week six of the evaluation. By the sixth week following application, formulation II demonstrates greater control over the Oriental fruit flies in the area of the traps than formulation I. The letters above the columns in FIG. 1 representing the data collected at week 6 indicate that the number of flies trapped using formulation II in week 6 were statistically significantly higher than the number of flies trapped using formulation I, including methyl eugenol alone. So even though there was an equal amount of methyl eugenol in the 2 g dollop of formulation I and the 4 g dollop of formulation II, formulation II was significantly better at controlling Oriental fruit flies than formulation I in the sixth week of the test. This is a surprising and unexpected result in view of the published literature reporting prior experiments in which cue lure was shown to have an inhibitory or antagonistic effect on the ability of methyl eugenol to attract Oriental fruit flies.

While multiple embodiments of the invention have been described in detail in the foregoing description, the same is to be considered as illustrative and not restrictive in character, it being understood that only the selected embodiments have been described and that all changes, modifications and equivalents that come within the spirit of the invention as defined herein or by any of the following claims are desired to be protected. Any theory, mechanism of operation, proof, or finding stated herein is meant to further enhance understanding of the present disclosure and is not intended to make the present disclosure in any way dependent upon such theory, mechanism of operation, proof, or finding. It should be understood that any use of the word preferable, preferably or preferred in the description above indicates that the feature so described may be more desirable, it nonetheless may not be necessary and embodiments lacking the same may be contemplated as within the scope of the invention, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary. All patents, patent applications, and publications references herein are hereby incorporated by reference, each in its entirety.

What is claimed is:

1. An insect control formulation, comprising from 10% to 30% by weight of the total formulation of methyl eugenol; from 5% to 15% by weight of the total formulation of cue lure; and from 30% to 70% by weight of the total formulation of a biodegradable wax carrier as an emulsion comprising paraffin wax;
    wherein said methyl eugenol and said cue lure are dispersed in said biodegradable wax carrier;
    wherein said biodegradable wax carrier is operable to release the methyl eugenol and cue lure for at least four weeks; and
    wherein release of the methyl eugenol and cue lure is effective for attracting a cue lure responding melon fly and a methyl eugenol responding oriental fruit fly without antagonistically affecting attraction of the methyl eugenol responding oriental fruit fly.

2. The formulation in accordance with claim 1, further comprising from 0.2% to 10% by weight of the total formulation of an insecticide.

3. The formulation in accordance with claim 1, wherein the formulation further comprises water.

4. The formulation in accordance with claim 1, comprising from 15% to 25% by weight of the total formulation of said methyl eugenol.

5. The formulation in accordance with claim 1, further comprising from 0.002% to 25% by weight of the total formulation of an insecticide.

6. The formulation in accordance with claim 1, further comprising one or more additives selected from the group consisting of lipids, emulsifiers, plasticizers, UV blockers and absorbers, antimicrobials, antioxidants and volatility suppressants.

7. The formulation in accordance with claim 6, wherein the one or more additives is present in an amount from about 0.001% to about 20% by weight of the formulation.

8. The formulation in accordance with claim 6, wherein the additive is present in an amount from about 0.1% to about 10% by weight of the formulation.

9. The formulation in accordance with claim 6, wherein the additive is an emulsifier in an amount up to about 10% by weight of the formulation.

10. The formulation in accordance with claim 6, wherein the additive is an emulsifier selected from the group consisting of soy oil, lecithins, modified lecithins, monoglycerides, diglycerides, sorbitans, and fatty acids, and combinations thereof.

11. The formulation in accordance with claim 6, wherein the additive is an antioxidant in an amount of from about 0.1% to about 3% by weight of the formulation.

12. The formulation in accordance with claim 11, wherein the antioxidant is selected from the group consisting of vitamin E, butylated hydroxyanisole, and butylated hydroxytoluene.

13. The formulation in accordance with claim 6, further comprising spinosad.

14. The formulation in accordance with claim 2, wherein the insecticide comprises spinosad.

15. A method of insect control comprising:
   identifying a locus where control of oriental fruit flies and melon fruit flies is desired;
   placing at the locus the formulation of claim 1, wherein the formulation further comprises from 0.2% to 10% by weight of the formulation of an insecticide.

16. The method of claim 15, wherein the insecticide comprises spinosad.

* * * * *